(12) United States Patent
Le Cain et al.

(10) Patent No.: US 11,815,744 B2
(45) Date of Patent: Nov. 14, 2023

(54) METHOD FOR DETERMINING A POSTURAL AND VISUAL BEHAVIOR OF A PERSON

(71) Applicant: Essilor International, Charenton-le-Pont (FR)

(72) Inventors: Aurelie Le Cain, Charenton-le-Pont (FR); Sebastien Fricker, Charenton-le-Pont (FR)

(73) Assignee: Essilor International, Charenton-le-pont (FR)

( * ) Notice: Subject to any disclaimer, the term of this patent is extended or adjusted under 35 U.S.C. 154(b) by 490 days.

(21) Appl. No.: 16/631,674

(22) PCT Filed: Jul. 18, 2018

(86) PCT No.: PCT/EP2018/069508
§ 371 (c)(1),
(2) Date: Jan. 16, 2020

(87) PCT Pub. No.: WO2019/016267
PCT Pub. Date: Jan. 24, 2019

(65) Prior Publication Data
US 2020/0249498 A1 Aug. 6, 2020

(30) Foreign Application Priority Data
Jul. 18, 2017 (EP) ..................................... 17305955

(51) Int. Cl.
*G02C 7/02* (2006.01)
*G06T 7/70* (2017.01)
(Continued)

(52) U.S. Cl.
CPC ............ *G02C 7/027* (2013.01); *A61B 3/0025* (2013.01); *A61B 3/113* (2013.01); *A61B 3/145* (2013.01);
(Continued)

(58) Field of Classification Search
CPC ... A61B 2576/00; A61B 3/0025; A61B 3/113; A61B 3/145; A61B 5/0077;
(Continued)

(56) References Cited

U.S. PATENT DOCUMENTS 7,742,623 B1 6/2010 Moon et al.
10,303,250 B2 * 5/2019 Jeong .................... G06T 19/006
(Continued)

FOREIGN PATENT DOCUMENTS

CN 110892311 A 3/2020
JP 2015-515291 A 5/2015

OTHER PUBLICATIONS

International Search Report and Written Opinion dated Oct. 18, 2018 in PCT/EP2018/069508 filed Jul. 18, 2018.
Japanese Office Action dated Jul. 11, 2022 in Japanese Patent Application No. 2020-502369 (with English translation), 11 pages.

*Primary Examiner* — Farzana Hossain
(74) *Attorney, Agent, or Firm* — Oblon, McClelland, Maier & Neustadt, L.L.P.

(57) ABSTRACT

A method for determining a postural and visual behavior of a person, the method comprising:—a person image receiving step during which a plurality of images of the person are received,—a context determining step during which the plurality of images of the person are analyzed so as to determine context data representative of the context in which the person is on each image of the plurality of images,—an analyzing step during which the plurality of images of the person are analyzed so as to determine at least one oculomotor parameter of the person,—a postural and visual behavior determining step during which a postural and visual behavior of the person is determined based at least on the at least one oculomotor parameter and the context data.

18 Claims, 2 Drawing Sheets

(51) Int. Cl.
*A61B 3/00* (2006.01)
*A61B 3/113* (2006.01)
*A61B 3/14* (2006.01)
*A61B 5/00* (2006.01)
*A61B 5/11* (2006.01)

(52) U.S. Cl.
CPC .......... *A61B 5/0077* (2013.01); *A61B 5/1116* (2013.01); *A61B 5/1128* (2013.01); *G02C 7/025* (2013.01); *G06T 7/70* (2017.01); *A61B 2576/00* (2013.01); *G06T 2207/30* (2013.01); *G06T 2207/30004* (2013.01); *G06T 2207/30041* (2013.01)

(58) Field of Classification Search
CPC ..... A61B 5/1116; A61B 5/1128; G02C 7/025; G02C 7/027; G06T 2207/30; G06T 2207/30004; G06T 2207/30041; G06T 7/70
See application file for complete search history.

(56) References Cited

U.S. PATENT DOCUMENTS

| | | |
|---|---|---|
| 2016/0299360 A1 | 10/2016 | Fonte et al. |
| 2017/0059886 A1 | 3/2017 | Fayolle et al. |
| 2018/0107662 A1* | 4/2018 | Lore ................ G06F 16/436 |
| 2019/0060602 A1* | 2/2019 | Tran ..................... G06F 3/013 |
| 2019/0212581 A1* | 7/2019 | Scherlen ............... A61B 3/063 |
| 2020/0069172 A1* | 3/2020 | Perrin ................... A61B 3/028 |

\* cited by examiner

METHOD FOR DETERMINING A POSTURAL AND VISUAL BEHAVIOR OF A PERSON

FIELD OF THE INVENTION

The invention relates to a method for determining a postural and visual behavior of a person, to an optical lens adapted for a person obtained by the method of the invention, to a programmable optical lens whose optical function is adapted based on the optical function obtained by a method of the invention, and to a computer program product comprising one or more stored sequences of instructions corresponding to the method of the invention.

BACKGROUND OF THE INVENTION

Usually, a person wishing to have an eyewear equipment goes to an eye care practitioner.

The eye care practitioner orders the eyewear equipment at an optical lab by sending an order request to the optical lab. The order request comprises person data, for example the person's prescription, spectacle frame data, for example the type of spectacle frame the person has selected, and lens data, for example the type of optical lens the person has selected.

The optical lab receives the order request and sends it to an optical lens designer software. The lens designer software uses some of the data comprised in the order request to calculate the design of the optical lenses to be provided to the person. The optical design determined by the lens designer software is sent to the optical lab and the optical lenses are manufactured based on the calculated design.

The manufactured optical lenses can be processed to add the optical treatments according to the order request.

The optical lenses are then sent to the eye care practitioner. The optical lenses may be edged to fit the spectacle frame prior to being sent to the eye care practitioner and mounted on the spectacle frame.

The current optical lens delivering process presents some drawbacks.

In the recent years, new optical designs have been invented. These new optical designs are more and more customized according to the person. To calculate such customized optical designs the lens designer needs more and more data relative to the person. The wording "optical design" designates the set of parameters allowing defining a dioptric function of an ophthalmic lens. Generally, the data relating to the person are measured or evaluated in very standard environment. Typically, the eye care professional carries out a set of standard tests corresponding to the average situation. For example, when determining far vision prescription, the eye care professional has the person under test recognizing letters at a distance of about 5 meters.

When determining the near vision prescription, the eye care professional may have the wearer read a text at about 40 cm.

Usually, most of the vision tests are not customized.

An example, of a customizing of an optical function is considering the relative head and eye movements of the person when looking at blinking lights to adapt the optical function to be provided as disclosed in the patent application EP1834206.

The measurements of the relative movements of the head and eyes of the person are usually carried out in a standard environment, for example an eye care professional lab.

As illustrated the determination of most of the wearer parameters are done in very standard environment.

Recent developments in optical designs, allow a much greater customization of the optical functions to a point where customizing the conditions in which the parameters are determined may have an impact of the optical function.

Therefore, there is a need for a method for determining customized parameters such as the postural and visual behavior of a person and that is easy and quick to implement.

One object of the present invention is to provide such method.

SUMMARY OF THE INVENTION

To this end, the invention proposes a method for determining a postural and visual behavior of a person, the method comprising:

a person image receiving step during which a plurality of images of the person are received, a context determining step during which the plurality of images of the person are analyzed so as to determine context data representative of the context in which the person is on each image of the plurality of images, an analyzing step during which the plurality of images of the person are analyzed so as to determine at least one oculomotor parameter of the person, and a postural and visual behavior determining step during which a postural and visual behavior of the person is determined based at least on the at least one oculomotor parameter and the context data.

Advantageously, the method of the invention allows determining a postural and visual behavior based on oculomotor parameter of a person determined in relation with a context. Typically, the oculomotor parameters are determined in different visual environment or while having the person carry out different or specific activities.

The images of the person may typically be images provided by the person itself and representative of the context in which the person is most of the time or for which the person wishes to have a specific optical function.

For example, if the person likes to play chess outside, the image received in the method of the invention may be images of said person playing chess outside. Oculomotor parameters may be determined based on the provided images and used to determine for a postural and visual behavior of the person. Advantageously, the oculomotor parameters are determined in a "real-life" context allowing an accurate determination of the postural and visual behavior. Furthermore, the method of the invention allows comparing evolution of oculomotor parameters over time if images corresponding to different time in the life of the person are received.

Additionally, the method of the invention allows determining a lens utilization anomaly such as an inappropriate utilization of optical lenses and/or utilization of optical lenses not adapted for the person based on the postural and visual behavior.

Furthermore, the method of the invention allows determining an optical function adapted for the wearer based on the postural and visual behavior.

According to further embodiments which can be considered alone or in combination:

the method further comprises:
 a reference postural and visual behavior data receiving step during which reference postural and visual behavior data are received, the reference postural and visual behavior data corresponding to the appropriate postural and visual behavior of a reference person wearing lenses of a specific prescription adapted to said reference person, and a comparison step during which reference postural and visual behavior data and the postural and visual behavior of the person are compared so as to determine a lens utilization anomaly, the lens utilization anomaly referring to an inappropriate utilization of the lenses and/or the utilization of lenses not adapted for the person; and/or the method further comprises a prescription data receiving step during which prescription data of the person are received, and an optical function determining step during which an optical function adapted for the wearer is determined based at least on the prescription data and the postural and visual behavior of the person; and/or the optical function is adapted for the person in at least one context; and/or during the optical function determining step a dioptric function adapted for the person is determined; and/or during the optical function determining step an electrochromic function adapted for the person is determined; and/or plurality of images of the person received during the person image receiving step are received from at least one distant image data base; and/or the plurality of images of the person received during the person image receiving step comprises at least part of the person's face, for example at least the person's eyes; and/or the plurality of images of the person received during the person image receiving step comprise static images and/or videos of the person; and/or the at least one oculomotor parameter relates at least to the gazing direction of the person; and/or the at least one oculomotor parameter relates at least to the gazing distance of the person; and/or the at least one oculomotor parameter relates at least to the position and orientation of the head of the person; and/or the context data relate to the activity carried out by the person on the images; and/or the context data relate to the visual environment of the person on the images; and/or the method further comprises:

prior to the context determining step a context data receiving step during which context data representative of the at least one context are received, and further to the context determining step an image selection step during which a plurality of images of the at least one person in the at least one context are selected, during the analyzing step the selected plurality of images of the at least one person are analyzed; and/or the method further comprising prior to the context determining and analyzing steps an image selection step during which the images of the person wearing single vision ophthalmic lenses or no ophthalmic lenses are selected and the context determining and analyzing steps are carried out on the selected images; and/or the method further comprises an optical function sending step during which the optical function determined during the optical function determining step is sent to a programmable lens device controller arranged to control the optical function of a programmable lens; and/or the method further comprises a manufacturing step during which an optical lens having the optical function determined during the optical function determining step is manufactured.

The invention also relates to a method of manufacturing an ophthalmic lens for a person, the method comprising:

an optical function determining step during which the optical function of the ophthalmic lens is determined using a method according to the invention, and a manufacturing step during which the optical lens is manufactured.

The invention further relates to an optical lens adapted for a person obtained by the method according to the invention.

The invention further relates to a computer program product comprising one or more stored sequences of instructions that are accessible to a processor and which, when executed by the processor, causes the processor to carry out at least the steps of the method according to the invention.

The invention also relates to a computer-readable storage medium having a program recorded thereon; where the program makes the computer execute at least the steps of the method of the invention.

The invention further relates to a device comprising a processor adapted to store one or more sequence of instructions and to carry out at least steps of the method according to the invention.

BRIEF DESCRIPTION OF THE DRAWINGS

Embodiments of the invention will now be described, by way of example only, and with reference to the following drawings in which.

DETAILED DESCRIPTION OF PREFERRED EMBODIMENTS

Figure 1:
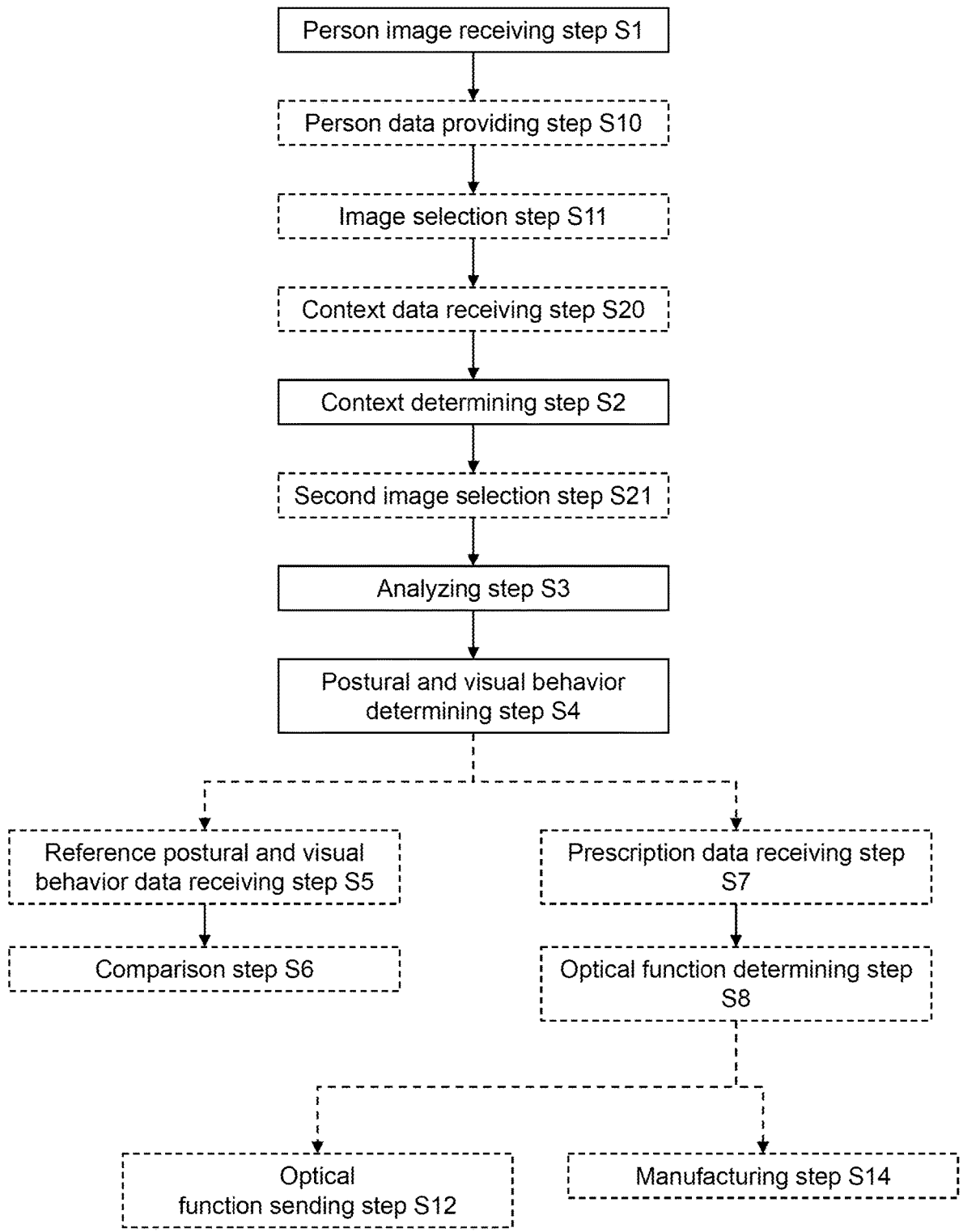
FIG. 1 is a flow chart representing a method according to the invention.
Figure 2:
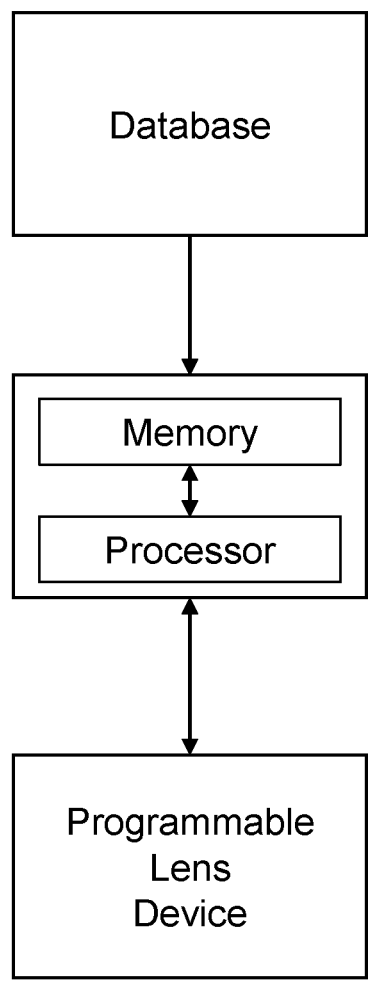
FIG. 2 provides an example of an embodiment of the disclosure.

As illustrated on FIG. 1, the method for determining a postural and visual behavior of a person according to the invention comprises:

a person image receiving step S1,
a context determining step S2,
an analyzing step S3,
a postural and visual behavior determining step S4.

During the person image receiving step S1 a plurality of images of the person are received.

The images received during the person image receiving step may be received from a distant image data base.

For example, the method may comprise connecting to a distance image data base, for example to a social network data base, to receive image of the person.

Typically, the person allows access to images and/or videos of him available on at least one social network or personal data base.

The person may also provide the images via a storage medium, such as a hard drive, USB key, DVD, Blu-ray, or any known storage mean.

The images received during the image receiving step may comprise static images such as pictures and/or videos. The images may be 2-dimensional images or 3-dimensional images further comprising depth information.

So as to increase the accuracy of the method, preferably, at least part of the person's face is visible on the images provided during the image providing step. For example, at least the person's eyes are visible on the images.

The method of the invention may further comprise a person data providing step S10 during which person data related to the person are provided. The person data may comprise information concerning for example the type, shape, dimension of spectacle frame the person has selected and/or the person interpupillary distance and/or wearing condition parameters or any information concerning the person that may be useful for determining the postural and visual behavior of the person.

As illustrated on FIG. 1, the method of the invention may further comprise an image selection step S11. During the image selection step S11, at least part of the images provided are selected.

For example, the images comprising at least part of the person's face, such as the person's eyes, are selected.

Images of the person wearing single vision ophthalmic lenses or no ophthalmic lenses may be selected during the image selection step.

The image selection step may be based on information provided with the images. For example, each image may comprise an indication of the date on which the image was taken. Knowing the date on which the person has started to wear progressive ophthalmic lenses, the image selection step may comprise selecting image based on their date, keeping only the images prior to the date on which the person started wearing progressive ophthalmic lenses.

The image selection step may comprise image analyzing to identify the person on the pictures.

For example, to check that at least part of the person's face is on the images, the images are analyzed to detect faces on the image. For example, one may use the face detection method disclosed in U.S. Pat. No. 6,697,502.

To check that the face detected in the one of the person one may use a facial recognition method, for example the method disclosed in W.Y. Zhao, R. Chellappa, Image-based Face Recognition: Issues and Methods, Image Recognition and Classification, Ed. B. Javidi, M. Dekker, 2002, pp. 375-402.

The method may comprise noise reduction for the image selected.

During the context determining step S2 the plurality of images of the person are analyzed so as to determine context data representative of the context in which the person is on each image of the plurality of images.

The context determining step may comprise face recognition, in particular if such face recognition is not part of the image selection step.

The context data may relate to the activity carried out by the person on the images.

For example, the context data may identify directly an activity carried out by the person or may be data allowing determining such activity, for example an indication allowing determining the activity of the person from a data base and/or lookup table.

The person activity data may be provided directly by the person itself, for example by selecting an activity in a list of activities.

Furthermore, the person activity data may be determined based on analysis of the images.

The activity that may be identified may be for example, but not limited to driving, sport, playing golf, playing tennis, practicing archery, reading, walking, paragliding, etc. . . .

Most researchers in HAR (Human Activity Recognition) use supervised classification algorithms. The algorithms are trained with labeled samples to generate classification model. Then the model is used for classification of input data. From the survey, the most popular algorithms are Decision Trees, k-Nearest Neighbor, Naïve Bayes, Support Vector Machine and Neural Network.

An example a human activity recognition method is described in SULONG, GHAZALI, and AMMAR MOHAMMEDALI. "RECOGNITION OF HUMAN ACTIVITIES FROM STILL IMAGE USING NOVEL CLASSIFIER." Journal of Theoretical & Applied Information Technology 71.1 (2015).

The context data may relate to the visual environment of the person on the images.

For example, the context data may relate to any parameter of the environment of the person on the images that may have an impact on the visual behavior of the person.

For example, the context data may relate to spectral features and intensity of the light received by the person on the images.

Furthermore, the context data may relate to temperature and/or humidity of the environment of the person, the amount and/or the type of allergens and/or pollutants contained in the environment of the person and/or an indication of the localization of the person such as indoor or outdoor and/or the place of carrying out the activity of the person, proximity to relief and/or water, etc . . .

During the analyzing step S3 the plurality of images are analyzed so as to determine at least one oculomotor parameter of the person.

The oculomotor parameters of the person may comprise as eye movements for example gaze lowering, and/or saccades for example head-eye coordination, and/or convergence and/or opening of the eyelid and/or pupil diameter and/or blink frequency and/or duration of the blink and/or strength of the blink and/or the position and/or orientation of the head of the person, for example reading distance.

The data collected during the analyzing step can be post treated to determine further information such as the dominant eye of the person or identify the area of the optical lens that is the most used by the person depending on the type of activity of the person and/or the environment of the person.

For example, for each image, the distance to the point observed by the person is evaluated, and then its proximity is determined. If the activity is far distance vision in this case proximity is set to be equal to 0.

To calculate a distance between two objects on a 2D image for which the context is known, the depth is taken into account.

Typically, to determine the distance between two elements on a 2 dimension image, such as an eye and an object, one performs a contour search to detect the contour of the two elements, then an Euclidean measurement between the barycenter's of the form of the two element is performed.

In order to calculate a distance that takes into account the depth of the image, a method may be used to obtain the 3D information and to convert the Euclidean distance. An example of such a method is disclosed in "From 2D TO 3D Through Modelling Based On A Single Image" by D. Gonzalez-Aguilera, The Photogrammetric Record 23(122): 208-227 (June 2008).

The method for determining distance may require knowing the size of element present in the image. For example, if both eyes of the person are present on the image and the interpupillary distance of the person is known it may be used as a reference element.

Any element of known size, such as a credit card, a spectacle frame, a smartphone present in the image may be used as reference element for calculating distance.

Therefore, the method of the invention may further comprise identifying an element of known dimension in the images provided.

In addition to the gazing distance, the head angles of the person and the direction of gaze may be evaluated in the images.

For example, the person's posture may be determined using the method disclosed in US20070268295, the head angles may be deduced therefrom.

The gazing direction may be determined using the method disclosed in Gaze direction estimation from static images; Krystian Radlak; Michal Kawulok; Bogdan Smolka; Natalia Radlak; Multimedia Signal Processing (MMSP), 2014 IEEE 16th International Workshop.

During the postural and visual behavior determining step S4, a postural and visual behavior of the person is determined based at least on the at least one oculomotor parameter and the context data.

As illustrated on FIG. 1, the method of the invention may further comprises a reference postural and visual behavior data receiving step S5 during which reference postural and visual behavior data are received. The reference postural and visual behavior correspond to the appropriate postural and visual behavior of a person wearing optical lenses of a specific prescription adapted to said reference person.

The reference postural and visual behavior may correspond to the appropriate postural and visual behavior of a person carrying out a specific activity and wearing optical lenses of a specific prescription adapted for said specific activity.

During the comparison step S6 the reference postural and visual behavior data and the postural and visual behavior of the person are compared so as to determine an optical lens utilization anomaly.

The lens utilization anomaly refers to an inappropriate utilization of optical lenses and/or to the utilization of optical lenses not adapted for the person.

As illustrated on FIG. 1, the method of the invention may further comprises a prescription data receiving step S7.

During the prescription data receiving step prescription data relating to the prescription of the person are received.

The prescription of the person is a set of optical characteristics of optical power, of astigmatism and, where relevant, of addition, determined by an ophthalmologist in order to correct the vision defects of the person, for example by means of a lens positioned in front of its eye. For example, the prescription for a progressive addition lens comprises values of optical power and of astigmatism (modulus and axis) at the distance-vision point and, where appropriate, an addition value.

For example, the prescription of the person may be the prescription of an emmetropic person.

During the optical function determining step S8 an optical function adapted for the person is determined based at least on the prescription data and the postural and visual behavior of the person.

The optical function determination may comprise selecting the most appropriate optical function in a predefined list of optical function.

The selected optical function may then be customized based on the prescription data, the at least one oculomotor parameter and the context data.

According to an embodiment of the invention, the optical function may be determined using optimization algorithms based on the prescription data and the postural and visual behavior of the person.

In the sense of the invention, the optical function corresponds to a function providing for each gaze direction the effect of the optical lens on the light ray passing through the optical lens.

The optical function may comprise dioptric function, electrochromatic function, light absorption, polarizing capability, reinforcement of contrast capacity, etc . . .

The dioptric function corresponds to the optical lens power (mean power, astigmatism etc . . . ) as a function of the gaze direction. The dioptric function may be optimized using the method according to the invention.

For example, if the ophthalmic lens to be provided to the person is a progressive addition lens the method according to the invention may be used to optimize various parameters of the optical function among which the relative positions of the near and far vision zones and/or the type of design and/or the length of progression and/or the size of the progressive corridor and/or the widths of the different vision zones.

In the sense of the invention a progressive addition lens is an ophthalmic lens having a far vision zone, a near vision zone, and a progressive corridor (or channel) there between. The progressive corridor provides a gradual power progression from the far vision zone to the near vision zone without dividing line or prismatic jump.

In the sense of the invention the length of progression of a progressive addition lens corresponds to the distance measured vertically (in worn conditions) over the lens surface between the fitting cross and a point on the meridian line at which the mean sphere has a difference of 85% relative to the mean sphere at the far vision point.

The wording "optical design" is a widely used wording known from the man skilled in the art in ophthalmic domain to designate the set of parameters allowing defining a dioptric function of an ophthalmic lens; each ophthalmic lens designer has its own designs, particularly for progressive ophthalmic lenses. As for an example, a progressive ophthalmic lens "design" results of an optimization of a progressive surface so as to restore a presbyope's ability to see clearly at all distances but also to optimally respect all physiological visual functions such as foveal vision, extra-foveal vision, binocular vision and to minimize unwanted astigmatisms. For example, a progressive lens design comprises:

a power profile along the main gaze directions (meridian line) used by the lens wearer during day life activities, distributions of powers (mean power, astigmatism, . . . ) on the sides of the lens, that is to say away from the main gaze direction.

These optical characteristics are part of the "designs" defined and calculated by ophthalmic lens designers and that are provided with the progressive lenses. For example, it is possible to detect if the person is in a category of eye mover or a category of head mover, or any intermediate category, by measuring the range of gazing direction of the eyes (horizontal or vertical).

Then, if the person is of a category of eye mover, a progressive hard design is proposed, whereas if the wearer is head mover, a soft design is proposed, whereas a tradeoff between hard/soft designs is to be proposed for intermediate category.

The category can be determined based on the minimum/maximum or the variance of the gaze direction.

The size of the area of an optical lens to be provided to the person may also be optimized with the method according to the invention. Indeed, the method according to the invention can provide information on the size of the area of an optical lens used by the person. Each person may use area of different size, therefore the size of the optical lens may be adjusted to correspond to the needs of the person.

The optimization of the optical lens may consist in optimizing the position of the optical lens in the spectacle frame. In particular the position of a reference point of the optical lens, such as the prism reference point, relative to the eye of the person may be optimized by a method according to the invention.

For example, it is possible to determine in different context the gaze direction for far vision, take the average gaze direction, determine the impact of this average gaze direction with the frame shape and then position the fitting cross of a progressive lens at this location.

According to an embodiment of the invention the transmission function of the optical lens can be optimized. In the sense of the invention the transmission function corresponds to a function providing for each gaze direction the average transmission over a range of wavelength. The average transmission over a range of wavelength corresponds to the percentage of intensity of the incident light within the corresponding range of wavelength that is transmitted through the optical system.

For example, the context data may be used to propose different transmission function, for example category between 0-4 (ISO8980-3) adapted to the person's environment, or to propose specific UV cut-off solution, for example Crizal UV AR coatings, or polarized lenses.

According to an embodiment of the invention, the optical function determining step can take the form of a prescription of specific types of lenses to the person. For example, if the analyzing step shows frequent watering of the eye to reddish glow revealing visual fatigue, lens reducing visual strength can be proposed to the person. An example of lens is Essilor antifatigue™.

According to an embodiment of the invention, the method according to the invention can be used to optimize classic optical lenses that are manufactured and edged to fit in a spectacle frame, for example the same type of spectacle frame as the person is wearing on the images.

According to an embodiment of the invention, the optical function is adapted for the person in at least one context.

As illustrated on FIG. 1, the method may further comprise prior to the context determining step a context data receiving step S20.

During the context data receiving step S20, context data representative of the at least one context, for example corresponding to a choice of the person, are received.

During a second image selection step S21, the images corresponding to the context data are selected. The plurality of images of the at least one person in the at least one context are analyzed during the analyzing step.

Advantageously, the optical function is optimized to a specific context for example for a specific activity and/or a specific visual environment.

The invention also relates to a method of manufacturing an ophthalmic lens for a person, the method comprising:
an optical function determining step during which the optical function of the ophthalmic lens is determined using a method according to the invention, and
a manufacturing step S14 during which the optical lens is manufactured.

The invention also relates to the optical lens adapted for a person obtained by the method of the invention.

Alternatively, the optimization method according to the invention can be used to optimize the optical function of an adjustable lens, for example a programmable lens.

Therefore, the method of the invention may further comprise an optical function sending step S12 during which the optical function determined during the optical function determining step is sent to a programmable lens device controller arranged to control the optical function of a programmable lens.

The invention has been described above with the aid of embodiments without limitation of the general inventive concept; in particular the mounted sensing device is not limited to a head mounted device.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A method for determining a visual and postural behavior a person, the method comprising:
receiving a plurality of images of the person;
analyzing the plurality of images of the person are analyzed to determine context data representative of the context in which the person is on each image of the plurality of images;
analyzing the plurality of images of the person to determine at least one oculomotor parameter of the person;
determining optical and postural behavior of the person based at least on the at least one oculomotor parameter and the context data;
receiving reference postural and visual behavior data, the reference postural and visual behavior data corresponding to an appropriate postural and visual behavior of a reference person wearing lenses of a specific prescription adapted to said reference person; and
comparing reference postural and visual behavior data and the postural and visual behavior of the person to determine a lens utilization anomaly, the lens utilization anomaly referring to an inappropriate utilization of the lenses and/or utilization of lenses not adapted for the person,
wherein, prior to the context determining, the method further comprises receiving context data representative of at least one context,
wherein the context determining further includes selecting a plurality of images of at least one person in the at least one context, and
wherein, during the analyzing the plurality of images of the person to determine the at least one oculomotor parameter of the person, the method further comprises analyzing the selected plurality of images of the at least one person.

2. The method according to claim 1, further comprising:
receiving prescription data of the person, and
determining an optical function for a lens element adapted for a wearer based at least on the prescription data and the postural and visual behavior of the person.

3. The method according to claim 2, wherein the optical function is adapted for the person in at least one context.

4. The method according to claim 2, wherein during the determining the optical function a dioptric function adapted for the person is determined.

5. The method according to claim 2, wherein during the determining the optical function an electrochromic function adapted for the person is determined.

6. The method according to claim 1, wherein the plurality of images of the person are received from at least one distant image data base.

7. The method according to claim 1, wherein the plurality of images of the person comprises at least part of the person's face.

8. The method according to claim 1, wherein the plurality of images of the person comprises static images and/or videos of the person.

9. The method according to claim 1, wherein the at least one oculomotor parameter relates at least to the gazing direction of the person.

10. The method according to claim 1, wherein the at least one oculomotor parameter relates at least to the gazing distance of the person.

11. The method according to claim 1, wherein the at least one oculomotor parameter relates at least to the position and orientation of the head of the person.

12. The method according to claim 1, wherein the context data relate to the activity carried out by the person on the images.

13. The method according to claim 1, wherein the context data relate to the visual environment of the person on the images.

14. The method according to claim 1, further comprising:
prior to the analyzing the plurality of images of the person to determine the context data representative of the context in which the person is on each image of the plurality of images and analyzing the plurality of images of the person to determine at least one oculomotor parameter of the person, selecting the images of the person wearing single vision ophthalmic lenses or no ophthalmic lenses are selected,
wherein the analyzing the plurality of images of the person to determine the context data representative of the context in which the person is on each image of the plurality of images and analyzing the plurality of images of the person to determine at least one oculomotor parameter of the person are carried out on the selected images.

15. A non-transitory computer program product comprising one or more stored sequences of instructions that are accessible to a processor and which, when executed by the processor, causes the processor to carry out the steps of the method according to claim 1.

16. The method according to claim 1, wherein the plurality of images of the person comprises at least part of the person's eyes.

17. The method according to claim 1, wherein the appropriate postural and visual behavior of the reference person wearing lenses of the specific prescription adapted to said reference person is postural and visual behavior that results in an optical purpose of the specific prescription being performed as intended according to a predetermined design of the lens having the specific prescription.

18. A method for providing an optical lens adapted for a person having an optical function, comprising:
providing a plurality of images of the person;
analyzing the plurality of images of the person to determine context data representative of the context in which the person is on each image of the plurality of images;
analyzing the plurality of images of the person to determine at least one oculomotor parameter of the person, the at least one oculomotor parameter relates at least to the position and orientation of the head of the person;
determining an optical and postural behavior of the person based at least on the at least one oculomotor parameter and the context data;
receiving prescription data of the person; and
determining the optical function for a lens element adapted for a wearer based at least on the prescription data and the optical and postural behavior of the person,
wherein, prior to the context determining, the method further comprises receiving context data representative of at least one context,
wherein the context determining further includes selecting a plurality of images of at least one person in the at least one context, and
wherein, during the analyzing the plurality of images of the person to determine the at least one oculomotor parameter of the person, the method further comprises analyzing the selected plurality of images of the at least one person.

* * * * *